US005843480A

United States Patent [19]

Miller et al.

[11] Patent Number: 5,843,480
[45] Date of Patent: Dec. 1, 1998

[54] CONTROLLED RELEASE DIAMORPHINE FORMULATION

[75] Inventors: Ronald Brown Miller, Basel, Switzerland; Stewart Thomas Leslie, Cambridge, England; Derek Allan Prater, Milton, England; Trevor John Knott, Wickford, England; Hassan Mohammad, Haslingfield, England

[73] Assignee: Euro-Celtique, S.A., Luxembourg, Luxembourg

[21] Appl. No.: 774,229

[22] Filed: Dec. 27, 1996

Related U.S. Application Data

[63] Continuation-in-part of Ser. No. 944,106, Sep. 29, 1997, which is a continuation of Ser. No. 343,630, Nov. 22, 1994, abandoned, and a continuation of Ser. No. 404,293, Mar. 14, 1995, abandoned.

[30] Foreign Application Priority Data

| Mar. 14, 1994 | [GB] | United Kingdom | 9404928 |
| Jun. 14, 1994 | [GB] | United Kingdom | 9411842 |
| Nov. 17, 1994 | [GB] | United Kingdom | 94308493 |
| Nov. 21, 1994 | [GB] | United Kingdom | 9423498 |

[51] Int. Cl.⁶ ............................................. A61K 9/14
[52] U.S. Cl. ........................ 424/484; 424/485; 424/486; 424/488; 424/489; 424/464; 424/468; 424/469; 424/470; 514/812
[58] Field of Search ................................ 424/484, 485, 424/486, 488, 489, 464, 468, 469, 470; 514/812

[56] References Cited

U.S. PATENT DOCUMENTS

| 2,738,303 | 3/1956 | Blythe et al. | 167/82 |
| 3,065,143 | 11/1962 | Christenson et al. | |
| 3,652,589 | 3/1972 | Flick et al. | |
| 3,830,934 | 8/1974 | Flick et al. | 424/330 |
| 3,845,770 | 11/1974 | Theeuwes et al. | 128/260 |
| 3,950,508 | 4/1976 | Mony et al. | 424/19 |
| 3,965,256 | 6/1976 | Leslie | 424/22 |
| 3,974,157 | 8/1976 | Shetty et al. | |
| 4,013,784 | 3/1977 | Speiser | 424/19 |
| 4,076,798 | 2/1978 | Casey et al. | 424/419 |
| 4,132,753 | 1/1979 | Blichare et al. | 264/25 |
| 4,259,314 | 3/1981 | Lowey | 424/19 |
| 4,343,789 | 8/1982 | Kawata et al. | 424/461 |
| 4,366,172 | 12/1982 | Lednicer | 424/330 |
| 4,380,534 | 4/1983 | Fukui et al. | 424/38 |
| 4,389,393 | 6/1983 | Schor et al. | 424/19 |
| 4,421,736 | 12/1983 | Walters | 424/19 |
| 4,483,847 | 11/1984 | Augart | 424/22 |
| 4,533,562 | 8/1985 | Ikegami et al. | 427/3 |
| 4,600,645 | 7/1986 | Ghebre-Sellassie et al. | 428/403 |
| 4,613,619 | 9/1986 | Sleigh et al. | 514/546 |
| 4,621,114 | 11/1986 | Watanabe | 524/451 |
| 4,728,513 | 3/1988 | Ventouras | 424/461 |
| 4,797,410 | 1/1989 | El-Fakahany | 514/356 |
| 4,801,458 | 1/1989 | Hidaka et al. | 424/443 |
| 4,801,460 | 1/1989 | Goertz et al. | 424/465 |

(List continued on next page.)

FOREIGN PATENT DOCUMENTS

| 2131350 | 3/1995 | Canada . |
| 0032004 | 12/1980 | European Pat. Off. . |
| 0097523 | 1/1984 | European Pat. Off. . |
| 0043254 | 5/1984 | European Pat. Off. . |
| 0108218 | 5/1984 | European Pat. Off. . |
| 0147780 | 7/1985 | European Pat. Off. . |
| 0152379 | 8/1985 | European Pat. Off. . |
| 0214735 | 7/1986 | European Pat. Off. . |
| 0189861 | 8/1986 | European Pat. Off. . |
| 0248548 | 5/1987 | European Pat. Off. . |
| 0249347 | 5/1987 | European Pat. Off. . |
| 0251459 | 5/1987 | European Pat. Off. . |
| 0253104 | 1/1988 | European Pat. Off. . |
| 0254978 | 2/1988 | European Pat. Off. . |
| 0256127 | 2/1988 | European Pat. Off. . |
| 0267702 | 5/1988 | European Pat. Off. . |
| 0271193 | 6/1988 | European Pat. Off. . |
| 0300897 | 7/1988 | European Pat. Off. . |
| 0295212 | 12/1988 | European Pat. Off. . |
| 0298355 | 1/1989 | European Pat. Off. . |
| 0327295 | 8/1989 | European Pat. Off. . |

(List continued on next page.)

OTHER PUBLICATIONS

Carter, S.J., et al., "Long–Acting Oral Medicaments", *Pharmacy Digest*, pp. 183–189, Apr. 1961.

Japanese Patent Publication No. 43 (1968) 20006 "Detailed Description of the Invention".

Bloomfield, et al., "Clinical Trials and Therapeutics—Analgesic efficacy and potency of two oral controlled–release morphine preparations", *Clinical Pharmacology & Therapeutics*, vol. 53, No. 4, pp. 469–478, Apr. 1993.

(Abstracts), 7th World Congress on Pain, Thursday, Aug. 26, 1993, Abstract Nos. 997–1001.

Multi–dose randomized crossover trial demonstrates Roxanol SR and MS Contin are bioequivalent, 1988 Roxane Laboratories, Inc.

Hunt, Thomas L., M.D., Ph.D., et al., "Comparison of the Pharmacokinetic Profiles of Two Oral Controlled–Release Morphine Formulations in Healthy Young Adults", *Clinical Therapeutics*, vol. 13, No. 4, pp. 482–488, 1991.

Thomsen, L., Juul, et al., "Prolonged Release Matrix Pellets Prepared by Melt Pelletization II. Hydrophobic Substances as Meltable Binders", *Drug Development and Industrial Pharmacy*, vol. 20, No. 7, pp. 1179–1197 (1994).

Thomsen, L., Juul, "Utilizing melt pelletization technique for the preparation of prolonged release products", *Pelletization*, (material elaborated by assistant prof. Lars Juul Thomsen, Department of Pharmaceutics, Royal Danish School of Pharmacy for the DIE course Pelletization Technology, Nov. 1992, 106 pages plus 3 appendices.

(List continued on next page.)

*Primary Examiner*—Nathan M. Nutter
*Attorney, Agent, or Firm*—Davidson, Davidson & Kappel, LLC

[57] ABSTRACT

A controlled-release pharmaceutical preparation comprising diamorphine, or a pharmaceutically acceptable salt thereof.

26 Claims, No Drawings

U.S. PATENT DOCUMENTS

| | | | |
|---|---|---|---|
| 4,828,836 | 5/1989 | Elger et al. | 424/419 |
| 4,834,984 | 5/1989 | Goldie et al. | 424/488 |
| 4,834,985 | 5/1989 | Elger et al. | 424/488 |
| 4,844,907 | 7/1989 | Elger et al. | 424/465 |
| 4,844,909 | 7/1989 | Goldie et al. | 424/480 |
| 4,861,598 | 8/1989 | Oshlack | 424/468 |
| 4,880,830 | 11/1989 | Rhodes | 424/470 |
| 4,894,234 | 1/1990 | Sharma et al. | 424/440 |
| 4,917,899 | 4/1990 | Geoghegan et al. | 424/19 |
| 4,925,675 | 5/1990 | Giannnini et al. | 424/78 |
| 4,935,246 | 6/1990 | Ahrens | 424/490 |
| 4,970,075 | 11/1990 | Oshlack | 424/451 |
| 4,987,136 | 1/1991 | Kreek et al. | |
| 4,990,341 | 2/1991 | Goldie et al. | 424/484 |
| 5,007,790 | 4/1991 | Shell | 424/451 |
| 5,019,397 | 5/1991 | Wong et al. | 424/473 |
| 5,023,089 | 6/1991 | Sakamoto et al. | 424/502 |
| 5,024,842 | 6/1991 | Edgren et al. | 424/473 |
| 5,026,560 | 6/1991 | Makino et al. | 424/494 |
| 5,030,400 | 7/1991 | Danielsen et al. | 264/101 |
| 5,068,110 | 11/1991 | Fawzi et al. | 424/461 |
| 5,071,646 | 12/1991 | Malkowska et al. | 424/497 |
| 5,073,379 | 12/1991 | Klimesh et al. | 424/467 |
| 5,126,145 | 6/1992 | Evenstad et al. | 424/465 |
| 5,132,142 | 7/1992 | Jones et al. | 427/196 |
| 5,133,974 | 7/1992 | Paradissis et al. | 424/480 |
| 5,162,117 | 11/1992 | Stupak et al. | 424/475 |
| 5,167,964 | 12/1992 | Muhammed et al. | 424/482 |
| 5,169,645 | 12/1992 | Shukla et al. | 424/499 |
| 5,178,868 | 1/1993 | Malmqvist-Granlund et al. | 424/490 |
| 5,196,203 | 3/1993 | Boehm | 424/490 |
| 5,202,128 | 4/1993 | Morella et al. | 424/469 |
| 5,204,119 | 4/1993 | Shiobara et al. | 424/489 |
| 5,266,331 | 11/1993 | Oshlack et al. | 424/468 |
| 5,271,934 | 12/1993 | Goldenberg et al. | 424/401 |
| 5,273,760 | 12/1993 | Oshlack et al. | 424/480 |
| 5,286,493 | 2/1994 | Oshlack et al. | 424/468 |
| 5,292,461 | 3/1994 | Juch et al. | 264/37 |
| 5,300,300 | 4/1994 | Egidio et al. | 424/456 |
| 5,321,012 | 6/1994 | Mayer et al. | 514/25 |
| 5,330,766 | 7/1994 | Morella et al. | 424/490 |
| 5,378,474 | 1/1995 | Morella et al. | 424/469 |
| 5,395,626 | 3/1995 | Kotwal et al. | 424/472 |
| 5,403,493 | 4/1995 | Mouche et al. | 424/489 |
| 5,403,593 | 4/1995 | Royce | 424/489 |
| 5,443,846 | 8/1995 | Yoshioka et al. | 424/498 |
| 5,453,283 | 9/1995 | Munch et al. | 424/489 |
| 5,472,710 | 12/1995 | Klokkers-Bethke et al. | 424/468 |
| 5,478,577 | 12/1995 | Suchler et al. | 424/489 |
| 5,500,227 | 3/1996 | Oshlack et al. | 424/476 |
| 5,549,912 | 8/1996 | Oshlack et al. | 424/468 |
| 5,591,452 | 1/1997 | Miller et al. | 424/468 |

FOREIGN PATENT DOCUMENTS

| | | |
|---|---|---|
| 0068450 | 1/1990 | European Pat. Off. |
| 0351580 | 1/1990 | European Pat. Off. |
| 0361680 | 4/1990 | European Pat. Off. |
| 0361910 | 4/1990 | European Pat. Off. |
| 0368247 | 5/1990 | European Pat. Off. |
| 0377517 | 7/1990 | European Pat. Off. |
| 0377518 | 7/1990 | European Pat. Off. |
| 0415693 | 3/1991 | European Pat. Off. |
| 0430287 | 6/1991 | European Pat. Off. |
| 0463833 | 6/1991 | European Pat. Off. |
| 0241615 | 9/1991 | European Pat. Off. |
| 0452145 | 10/1991 | European Pat. Off. |
| 0531611 | 4/1992 | European Pat. Off. |
| 0526862 | 2/1993 | European Pat. Off. |
| 0338383 | 3/1993 | European Pat. Off. |
| 0533297 | 3/1993 | European Pat. Off. |
| 0534628 | 3/1993 | European Pat. Off. |
| 0535841 | 4/1993 | European Pat. Off. |
| 0546676 | 6/1993 | European Pat. Off. |
| 0548448 | 6/1993 | European Pat. Off. |
| 0582380 | 2/1994 | European Pat. Off. |
| 0595311 | 5/1994 | European Pat. Off. |
| 0249347 | 6/1994 | European Pat. Off. |
| 0636370 | 2/1995 | European Pat. Off. |
| 0642788 | 3/1995 | European Pat. Off. |
| 0609961 | 8/1995 | European Pat. Off. |
| 0205282 | 9/1995 | European Pat. Off. |
| 0624366 | 5/1996 | European Pat. Off. |
| 2642420 | 3/1990 | France. |
| 1513166 | 6/1975 | Germany. |
| 3602360 | 7/1987 | Germany. |
| 3602370 | 8/1987 | Germany. |
| 3623193 | 1/1988 | Germany. |
| 4329794 | 3/1995 | Germany. |
| 0997399 | 4/1964 | United Kingdom. |
| 1405088 | 6/1971 | United Kingdom. |
| 1513166 | 6/1978 | United Kingdom. |
| 2030861 | 4/1980 | United Kingdom. |
| 2053681 | 2/1981 | United Kingdom. |
| 2111386 | 12/1982 | United Kingdom. |
| 2117239 | 3/1983 | United Kingdom. |
| 2196848 | 5/1988 | United Kingdom. |
| 2246514 | 2/1992 | United Kingdom. |
| 2281204 | 3/1995 | United Kingdom. |
| 2284760 | 6/1995 | United Kingdom. |
| WO9119484 | 12/1991 | WIPO. |
| WO9119485 | 12/1991 | WIPO. |
| 9201446 | 2/1992 | WIPO. |
| WO9202209 | 2/1992 | WIPO. |
| 9205774 | 4/1992 | WIPO. |
| 9206679 | 4/1992 | WIPO. |
| WO9222283 | 12/1992 | WIPO. |
| 9300076 | 1/1993 | WIPO. |
| 9304675 | 3/1993 | WIPO. |
| 9307859 | 4/1993 | WIPO. |
| WO9307861 | 4/1993 | WIPO. |
| 9310765 | 6/1993 | WIPO. |
| 9318753 | 9/1993 | WIPO. |
| WO9317667 | 9/1993 | WIPO. |
| 9324110 | 12/1993 | WIPO. |
| 9403160 | 2/1994 | WIPO. |
| 9403161 | 2/1994 | WIPO. |
| 9405262 | 3/1994 | WIPO. |
| 9422431 | 10/1994 | WIPO. |
| WO9423700 | 10/1994 | WIPO. |
| WO9514460 | 6/1995 | WIPO. |

OTHER PUBLICATIONS

Thomsen, L. Juul, "Prolonged Release Matrix Pellets Prepared by Melt Pelletization. Part IV: Drug Conent, Drug Particle Size, and Binder Composition", *Pharmaceutical Technology Europa*, pp. 19–22 (Oct. 1994).

Thomsen, L. Juul, et al., "Prolonged Release Matrix Pellets Prepared by Melt Pelletization I. Process Variables", *Drug Development and Industrial Pharmacy*, vol. 19, No. 15, pp. 1867–1887 (1993).

El–Shanaway, S., "Sustained Release of Nitrofurantoin From Inert Wax Matrixes", *J. Controlled Release*, vol. 26, vol. 1, Issued 1993, pp. 11–19.

Flanders, P., et al., "The Control of Drug Release From Conventional Melt Granulation Matrices", *Drug Development and Industrial Pharmacy*, vol. 13, No. 6, pp. 1001–1022 (1987).

McTaggart, C.M., et al., "The Evaluation of Formulation and Processing Conditions of a Melt Granulation Process", *Int. J. Pharm.*, vol. 29, No. 2, Issued 1984, pp. 139–146.

Schaefer, T., et al., "Melt granulation in a laboratory scale high shear mixer", *Drug Development and Industrial Pharmacy*, vol. 16, No. 8, pp. 1249–1277 (1990).

M. J. Jozwiakowski et al., "Characterization of a Hot–Melt Fluid Bed Coating Process for Fine Granules", Pharm. Resear., vol. 7, No. 11, 1990, pp. 1119–1124.

M. Niskanen et al., "Pelletization in a Centrifugal Granulator, Part I: Effects of Binder–Solution Concentration", Pharm. Tech. Int'l, Oct. 1990, pp. 22–38.

L. Lachman et al., "The Theory and Practice of Industrial Pharmacy", p. 315, Lea & Febiger, Phi. 1976.

FDA Guide to Inspections of Oral Solid Dosage Forms Pre/Post Approval Issues for Development and Validation, Jan. 1994.

T. Schaefer et al. "Melt Pelletization in a High Shear Mixer I Effects of Process variables and Binder", Acta Pharm. Nord. vol. 4, No.3, pp. 133–140, 1992.

T. Schaefer et al. "Melt Pelletization in a High Shear Mixer II Power Consumption and Granule Growth", Acta Pharm. Nord. vol. 4, No.3, pp. 141–148, 1992.

T. Schaefer, et al., "Melt Granulation in a Laboratory Scale High Shear Mixer", Drug Dev. and Indust. Phar., vol. 16, No. 8, pp. 1249–1277, 1990.

McTaggart, C.M. et al., "The Evaluation of Formulation and Processing Conditions of a Melt Granulation Process", Int'l. J. Pharm., vol. 19, No. 2, issued 1984, pp. 139–148.

El–Shanawany, S., "Sustained Release of Nitrofuration From Inert Wax Matrixes", J. Controlled Release, vol. 26, No. 1, issued 1993, pp. 11–19.

P. Flanders, et al., "The Controlled of Drug Releases From Conventional Melt Granulation Matrices", Drug Dev. and Industrial Pharm., vol. 13, No. 6, pp. 1001–1022, 1987.

Thomson, I. Juul, "Matrix Pellets Prolonged Formulations Prepared by Melt Pelletization", Dept. of Pharm. Royal Danish School of Pharmacy, 1992.

Thomsen, L. Juul, et al., "Prolonged Release Matrix Pellets Prepared by Melt Pelletization II. Hydrophobic Substances as Meltable Binders", Drug Development and Industrial Pharmacy, vol. 20, No. 7, pp. 1179–1197 (1994).

G.M. Crass et al., "Sustained and Controlled Release Drug Delivery Systems", Modern Pharmaceutics, 2nd Edition, pp. 635–671, 1990.

N. Follonier et al., "Evaluation of Hot–Melt Extrusion as a New Technique for the Production of Polymer–Based Pellets for Sustained Release Capsules Containng High Loadings of Freely Soluble Drugs", Drug Dev. and Indus. Pharm., vol. 20, No. 8, pp. 1323–1339, 1994.

Sustained Release Medications, Noyes Data Corp., 1980.

M.A. Longer, "Sustained–Release Drug Delivery Systems", Remington's Pharm. Scie., 18th Edition, pp. 1676–1693, 1990.

M. Zahirul I. Khan, "Recent Trends and Progress in Sustained or Controlled Oral Delivery of Some Water Soluble Drugs: Morphine Salts, Diltiazem and Captopril", Drug Devl. and Indus. Pharm., vol. 21, No. 9, pp. 1037–1070, 1995.

J.P. Skelly, Scale–up of Immediate Release Oral Solid Dosage Forms, AAPS/FDA Workshop Committee, Pharmaceutical Technology, pp. 68–74, Apr. 1995.

SK Baveja et al., Int. J. Pharmaceutics, 41, (1988), pp. 55–62.

Formulating for Controlled Release with METHOCEL® Premium Cellulose Ethers, The Dow Chemical Company, 1989.

M S Vasquez et al., Drug Dev. & Ind. Pharmacy, 18(11&12), pp. 1355–1378 (1992).

L W S Cheong et al., Pharm. Res 9 (11) pp. 1510–1514 (1992).

Pharmazeutische Stoffliste 10. Auflage, p. 193, Nov. 1994.

Kuschinsky et al., *Kurzes Lehrbuch der Pharmakologie und Toxikolgie*, George Theime Verlag Stuttgart, New York 1987, pp. 270–273.

Rote Liste 1992, Entry No. 05020.

Derwent WPI C92–138727 Abstract JP 04/217 925 of 7 Aug. 1992.

Herbert P Fiedler: Lexicon der Hilfsstoffe, 3rd Ed., 1989, pp. 272–273.

Sucker et al., (Eds.), Pharmazeutische Technologie, Stuttgart, 1979, pp. 497–498.

DA Alderman, Int. J. Pharm. Tech. and Prod. Mfr., 5(3) pp. 1–9, 1984.

HE Huber et al., J. Pharm. Sci. 55(9) Sep. 1966, pp. 974–976.

Lin SY et al., Current Therapeutic Research 52(3), pp. 486–492, Sep., 1992.

Aqualon Technical Information Bulletin VC–585, 1991.

P Colombo, Advanced Drug Delivery Reviews, 11 (1993) pp. 37–57.

KV Ranga Rao et al., Int. J. Pharmaceutics, 48 (1988) pp. 1–13.

JE Hogan, Drug Dev. & Ind. Pharmacy, 15 (6 & 7), pp. 975–999 (1989).

JL Ford et al., Int. J. Pharmaceutics, 24 (1985) pp. 327–338.

PB Daly et al., Int. J. Pharmaceutics, 18 (1984) pp. 201–205.

H Lapidus et al., J. Pharm. Sci., 55(8), Aug. 1966, pp. 840–843.

H Lapidus et al., J. Pharm. Sci., 57(8), Aug. 1968, pp. 1292–1301.

Advertisement, MS Contin™ 1986, 1987 The Purdue Frederick C ompany.

Carstensen, J.T., "Pharmaceutical Principles of Solid Dosage Farms", Ch. 8 & 14, Technomic Publishing, Lancaster, P.A., 1993.

E.M.G. van Bommel, "Production and Evaluation of In Vitro Release Characteristics of Spherical Grandient Matrix Systems", Acta Phar., Technol., 3b (2), pp. 74–78, 1990.

CONTROLLED RELEASE DIAMORPHINE FORMULATION

This application is a continuation-in-part of U.S. application Ser. No. 08/944,106, filed Sep. 29, 1997, still pending, which is a file wrapper continuation of U.S. application Ser. No. 08/343,630, filed Nov. 22, 1994, now abandoned, and this application is a continuation of U.S. Ser. No. 08/404,293, filed Mar. 14, 1995 and now abandoned.

BACKGROUND OF THE INVENTION

This invention relates to controlled-release preparations containing pharmaceutically active ingredients and, in particular, a controlled-release preparation for oral use containing diamorphine or a pharmaceutically acceptable salt thereof.

Diamorphine, also known as diacetylmorphine or heroin, is an opiate prescribed for severe pain. The currently used pharmaceutical formulations in which it is an active ingredient include injections, elixirs, linctus, and powders (see Martindale, The Extra Pharmaceopoeia 30th Ed.) Because of its instability in the presence of water, the injection, elixirs and linctus must each be freshly prepared before use. Conventional granulating techniques for the preparation of controlled-release preparations are not possible because of the rapid degradation of diamorphine in the presence of water and consequently formulating with release control components to provide dosage forms such as capsules containing granules, or tablets formed from compressed granules by such techniques has not, heretofore, been possible. All known pharmaceutical preparations of this substance provide only for instant release.

It is desirable that there should be available to patients suffering from severe pain a diamorphine preparation which has reasonable storage stability, does not have to be freshly prepared before use, is easily self-administered and which has a duration of activity of about 12 hours or more, preferably about 24 hours, and accordingly needs to be administered only once or twice a day.

An additional need for such a formulation has existed for some years in the field of the treatment of drug addiction. It is the policy in certain countries to provide registered addicts with free access under controlled conditions, to diamorphine (heroin); the aim of such a policy being to remove such addicts as customers from the black market, but also to reduce the otherwise widespread practice of need sharing which has resulted in a rapid spread of HIV and hepatitis infection among addicts. Nonetheless, such a policy presently requires the provision of diamorphine for self-injection by addicts and requires considerable control and supervision. There is, therefore, a need for a controlled-release diamorphine preparation which would facilitate treatment according to such a policy.

SUMMARY AND OBJECTS OF THE INVENTION

It is an object of the present invention to provide controlled-release pharmaceutical preparation which comprises diamorphine or a pharmaceutically acceptable salt thereof.

It is also an object of the invention to provide a process for the manufacture of a sustained-release pharmaceutical preparation comprising diamorphine or a pharmaceutically acceptable salt thereof.

It is a further object of the invention is to provide a process for the manufacture of sustained-release multiparticulates, granules or controlled-release seeds containing diamorphine or a pharmaceutically-acceptable salt thereof.

Yet another object of the invention is to provide a method of treating a patient suffering from pain comprising administering to a patient controlled-release pharmaceutical preparation comprising diamorphine or a pharmaceutically-accepted salt thereof.

It is also an object of the invention to provide a method of treating a heroin addict by maintenance therapy which comprises administering to the addict a preparation containing an effective amount of diamorphine or a pharmaceutically acceptable salt thereof.

The above objects and others are achieved in the present invention, which relates in part to a pharmaceutical preparation comprising diamorphine or a pharmaceutically acceptable salt thereof, wherein the preparation provides controlled-release of diamorphine or a pharmaceutically acceptable salt thereof. In preferred embodiments, the pharmaceutical preparation is suitable for oral administration. In other preferred embodiments, the preparation includes a matrix. The matrix may include a hydrophobic fusible carrier. In still other preferred embodiments, the preparation is in the form of multiparticulates, granules, or controlled-release seeds including diamorphine incorporated in a controlled-release matrix. Preferably, the dosage form provides controlled-release of diamorphine such that the dosage form is suitable for 12 to 24 hourly administration. A preferred composition provides a pharmaceutically acceptable amount of diamorphine or a salt thereof to provide treatment to a patient for at least about 12 hours, and more preferably for about 24 hours.

Another aspect of the present invention is directed to a process for the manufacture of a sustained-release pharmaceutical preparation which includes mechanically working in a high shear mixer, a mixture of diamorphine or pharmaceutically active salt thereof in particulate form and a particulate, hydrophobic, fusible carrier or diluent having a melting point from 35° to 150° C., at a speed and energy input which allows the carrier or diluent to melt or soften whereby it forms a matrix of hydrophobic fusible carrier or diluent containing diamorphine or salt thereof dispersed therein. Optionally, a release modifying component comprising a water soluble, fusible material or a particulate, soluble or insoluble organic or inorganic material may be included.

Yet a further aspect of the invention is directed to a process for the manufacture of sustained-release multiparticulates, granules or controlled-release seeds containing diamorphine or a salt thereof which includes the steps of:

(a) mechanically working in a high-shear mixer, a mixture of diamorphine or salt thereof in particulate form and a particulate, hydrophobic, fusible carrier or diluent having a melting point from 35° to 150° C., at a speed and energy input which allows the carrier or diluent to melt or soften, whereby it forms agglomerates;

(b) breaking down from step (a) said agglomerates to give controlled-release seeds and particles.

Optionally, the process may include:

(c) continuing mechanically working optionally with a further addition of low percentage of the carrier or diluent; and (d) optionally repeating step (b) and possibly step (c) one or more, e.g., up to five times.

The process may also include breaking down the products from step (c) agglomerates to produce controlled-release seeds and particles.

In preferred embodiments, the product of either process set forth above are sieved or milled to obtain multiparticulates, granules, or controlled-release seeds, or particles of a desired size range. The particulates, granules, or controlled-seeds or particles may then be further processed to form solid dosage forms, e.g., tablets or capsules.

The invention is also directed to a method of treating a patient suffering from pain which includes administering to a patient a controlled-release pharmaceutical preparation as outlined above which comprises an effective amount of diamorphine or a pharmaceutically-accepted salt thereof.

Another aspect of the invention is directed toward a method of treating a heroin addict by maintenance therapy, including the step of administering to the heroin addict preparation as outlined above, which includes diamorphine or a pharmaceutically-accepted salt thereof.

DETAILED DESCRIPTION OF THE INVENTION

In its broadest aspect, the present invention provides a controlled-release, pharmaceutical preparation which comprises diamorphine or a pharmaceutically acceptable salt thereof as an active ingredient.

The preparation of the invention is preferably in the form of a tablet or multiparticulates comprising the diamorphine or pharmaceutically acceptable salt thereof incorporated in a controlled-release matrix, which matrix preferably comprises a hydrophobic, fusible carrier or diluent in which the diamorphine or salt thereof is incorporated.

A pharmaceutical preparation in accordance with the invention containing diamorphine or a salt thereof as an active ingredient suitable for once or twice-a-day dosing which is preferably obtained by incorporation of the diamorphine or salt in a matrix system comprising a hydrophobic, fusible binder and optionally a release modifying component may preferably have an in-vitro dissolution rate as measured by modified Ph. Eur. basket or Ph Eur. Paddle Method at 100 rpm in 900 ml aqueous buffer at pH 4.5 at 37° C. (phosphate or acetate buffer) as follows:

| TIME (HR) | % DIAMORPHINE RELEASED |
|---|---|
| 1 | 0–70 |
| 2 | <80 |
| 4 | 10–100 |
| 12 | 40–100 |
| 16 | 50–100 |

One preferred formulation in accordance with the invention has a dissolution rate as follows:

| TIME (HR) | % DIAMORPHINE RELEASED |
|---|---|
| 1 | 10–70 |
| 2 | 15–80 |
| 4 | 30–100 |
| 6 | 40–100 |
| 12 | 60–100 |
| 16 | 70–100 |

Yet another preferred formulation in accordance with the invention has a dissolution rate as follows:

| TIME (HR) | % DIAMORPHINE RELEASED |
|---|---|
| 1 | 0–50 |
| 4 | 10–80 |
| 8 | 30–100 |
| 12 | 40–100 |
| 16 | 50–100 |

The controlled-release preparation in accordance with the invention can, surprisingly, be produced without the use of water in a granulation step, or other process features leading to degradation of the diamorphine. As a result, the preparations in accordance with the invention are not only pharmaceutically acceptable but the products possess two important advantages in that they show long-term stability on storage, and also the dissolution rates are stable over a long period of time.

A preferred preparation in accordance with the invention shows, subject to experimental error, no change in diamorphine salt content, nor in 6-1-acetylmorphine (or salt) or morphine (or salt) content nor any change in in-vitro dissolution rate (as defined herein) after storage for three months and more preferably six months at 30° C.

The pharmaceutical preparation in accordance with the invention in one preferred form comprises multiparticulates which generally are spherical or spheroidal particles of a size capable of passing through a mesh of size about 0.1 to about 3.0 mm, preferably about 0.1 to about 2.0 mm, the multiparticulates preferably comprising a matrix of a hydrophobic, fusible release control material within which the diamorphine or a pharmaceutically acceptable salt thereof is dispersed.

The preparation may comprise a capsule, e.g., a hard capsule, containing multiparticulates as described above; another, preferred preparation may comprise a tablet comprising compressed multiparticulates, granulates or controlled-release seeds or particles.

We have found that the total amount of active ingredient in the composition may vary within wide limits, for example, from about 10% to about 75% by weight thereof.

The hydrophobic, fusible component should be a hydrophobic material such as a natural or synthetic wax or oil, for example hydrogenated vegetable oil or hydrogenated castor oil, and suitably has a melting point of from about 35° to about 150° C.

A release-modifying component, when a water soluble fusible material, is conveniently a polyethylene glycol and, when a particulate material, is conveniently a material such as dicalcium phosphate or lactose.

Incorporation of lower levels of diamorphine, for example, between about 10% and about 30% by weight, may necessitate inclusion of low levels of a release-modifying component, for example, about 5% to about 15% by weight polyethylene glycol 6000 to achieve a satisfactory in-vitro release rate. At higher drug loadings, for example, about 40% to about 75% by weight, it is envisaged that only incorporation of very small amounts of polyethylene glycol, for example, about 0.001 to about 1% by weight, would be required to modify the in-vitro release rate.

The present invention also provides a process for the manufacture of a sustained-release pharmaceutical preparation which, in one aspect, comprises mechanically working in a high-shear mixer, a mixture of diamorphine or pharmaceutically-active salt thereof in particulate form and a particulate, hydrophobic, fusible carrier or diluent having a melting point from about 35° to about 150° C. and, optionally, a release-modifying component comprising a water soluble, fusible material or a particulate, soluble or insoluble organic or inorganic material, at a speed and energy output which allows the carrier or diluent to melt or soften whereby it forms a matrix of hydrophobic, fusible carrier or diluent, containing diamorphine or salt thereof dispersed therein, e.g., in the form of multiparticulates or granules or agglomerates.

A preferred process for the manufacture of sustained-release multiparticulates or granules or controlled-release seeds or particles containing diamorphine or a salt thereof in accordance with the invention comprises:

(a) mechanically working in a high-shear mixer, a mixture of diamorphine or salt thereof in particulate form and a particulate, hydrophobic fusible carrier or diluent having a melting point from about 35° to about 150° C. and, optionally, a release modifying component comprising a water soluble fusible material, or a particulate soluble or insoluble organic or inorganic material at a speed and energy output which allows the carrier or diluent to melt or soften, whereby it forms agglomerates;

(b) breaking down agglomerates from (a) or product from step (c) to give controlled-release seeds or particles; and optionally (c) continuing mechanically working optionally with a further addition of low percentage of the carrier or diluent; and (d) optionally repeating step (b) and possibly (c) one or more, e.g., up to five times.

The agglomerates from step (a) may be large, irregularly shaped agglomerates.

The product from step (c) may be obtained as large, irregularly shaped agglomerates, or beads or spherical or spheroidal pellets. As indicated in (d), the product from step (c) may be returned and treated according to step (b) one or more times.

This process is capable of giving a high yield (over 80%) of multiparticulates in a desired size range, with a desired in-vitro release rate, and uniformity of release rate.

Resulting multiparticulates, granules or controlled-release seeds or particles may be sieved or milled to eliminate any oversize or undersized material then formed into the desired dosage units by, for example, encapsulation into hard gelatin capsules containing the required dose of the active substance.

The multiparticulates, or the granulates, agglomerates or controlled-release seeds or particles obtained from the respective steps of the process can, if desired, be compressed, as mentioned above, to form controlled-release tablets.

Preferably, diamorphine or salt thereof is used in an amount which results in multiparticulates containing between about 10% and about 75%, especially between about 45% and about 75% w/w active ingredient for a high dose product and between about 10% and about 45% for a low dose product.

Usually dosage units include about 10 mg to about 1000 mg of diamorphine or salt thereof, e.g., 20 mg; 500 mg; 40 mg and 200 mg.

In the preferred method of the invention, preferably all the drug is added in step (a) together with a major portion of the hydrophobic, fusible release control material used. Preferably, the amount of fusible, release control material added in step (a) is between about 25% and about 75% w/w, e.g., between about 25% and about 45% w/w of the total amount of ingredients added in the entire manufacturing operation, more preferably between about 30% and about 60%. e.g., between about 30% and about 40%.

Preferably, all the fusible release control material is added at stage (a).

Preferably, stage (a) of the process may be carried out in conventional high-shear mixers with a stainless steel interior, e.g., a Collette Vactron 75 or equivalent mixer. The mixture is processed until a bed temperature of about 40° C. is achieved and the resulting mixture acquires a cohesive granular texture, with particle sizes ranging from about 1–3 mm to fine powder in the case of non-aggregated original material. Such material, in the case of the embodiments described below, has the appearance of agglomerates which, upon cooling below 40° C., have structural integrity and resistance to crushing between the fingers. At this stage, the agglomerates are of an irregular size, shape and appearance.

The agglomerates are preferably allowed to cool. The temperature to which it cools is not critical and a temperature in the range of room temperature to about 45° C., e.g., about 20° C. to about 30° C. may be conveniently used.

The agglomerates are broken down by any suitable means which will comminute oversized agglomerates and produce a mixture of powder and small particles, preferably with a diameter under about 2 mm. It is currently preferred to carry out the classification using a Jackson Crockatt granulator using a suitable sized mesh, or a Comil with an appropriate sized screen. We have found that if too small a mesh size is used in the aforementioned apparatus, the agglomerates melting under the action of the beater or impeller will clog the mesh and prevent further throughput of mixture, thus reducing yield. A mesh size of about 12 or greater or a 094G Comil screen have been found adequate.

In a preferred method, the classified material is returned to the high shear mixer and processing continued. It is believed that this leads to a cementation of the finer particles into multiparticulates of uniform size range or into large, irregularly shaped agglomerates, which agglomerates may be milled, e.g., in a Comil or Jackson-Crocket.

In this process of the invention, the temperature of the mixing bowl throughout the mechanical working is chosen so as to avoid excessive adhesion of the material to the walls of the bowl. We have generally found that the temperature should be neither too high nor too low with respect to the melting temperature of the fusible material and it can be readily optimized to avoid the problems mentioned above. The same applies to the process of mechanically working a mixture of drug and particulate hydrophobic fusible carrier in a high speed mixture first mentioned above. For example, in the processes described below in the Examples, a bowl temperature of approximately 60° C. has been found to be satisfactory and avoid adhesion to the bowl.

In order to ensure uniform energy input into the ingredients in the high-shear mixer, it is preferred to supply at least part of the energy by means of microwave energy.

Energy may also be delivered through other means such as by a heating jacket or via the mixer impeller and chopper blades.

After the multiparticulates, granules or controlled-release seeds or particles have been formed, they may be sieved to remove any over- or undersized material and allowed to cool before or after sieving.

The resulting multiparticulates, granules or controlled-release seeds or particles may be used to prepare dosage units such as tablet or capsules in manners known per se. To product tablets in accordance with the invention, multiparticulates, granules or controlled-release seeds or particles produced as described above may be mixed or blended with the desired excipient(s), if any, using conventional procedures, e.g., using a Y-Cone or bin-blender and the resulting mixture compressed according to conventional tableting procedures using a suitably sized tableting tooling. Tablets can be produced using conventional tableting machines and, in the embodiments described below, were produced on a standard single punch F3 Manesty machine or Kilian RLE15 rotary tablet machine.

Generally speaking, we find that tablets formed by compression according to standard methods give very low in-vitro release rates of the active ingredient. We have found that the in-vitro release profile can be adjusted in a number of ways. For instance, a higher loading of the drug will be associated with increased release rates; the use of larger proportions of a water soluble, fusible material in the particulates or surface active agent in the tableting formulation will also be associated with a higher release rate of the active ingredient. Thus, by controlling the relative amount of these ingredients, it is possible to adjust the release profile of the active ingredient.

The present invention also comprehends a method of treating a patient suffering from pain by administering to the patient a preparation containing an effective amount of diamorphine or a pharmaceutically acceptable salt in accordance with the invention.

The present invention further comprehends a method of treating a person addicted to diamorphine (heroin), by maintenance therapy, which comprises administering to such a person a preparation containing an effective amount of diamorphine or pharmaceutically acceptable salt thereof in controlled-release form according to the present invention.

The administration of the two aforesaid methods of treatment comprises administration by a physician or staff, and self-administration.

Such administration will preferably be once or twice daily.

EXAMPLE 1

0.35 kg of particulate diamorphine hydrochloride and the same weight of particulate hydrogenated vegetable oil (LUBRITAB®) were placed in the bowl of a Collette Gral 10 or equivalent mixer, preheated to 60° C. Mixing was carried out at the following speeds for the Collette Gral 10—mixer 350 rpm; chopper 1500 rpm, until the contents of the bowl were slightly agglomerated. The agglomerates were then allowed to cool to approximately 40° C., and were milled in a Comil to obtain controlled-release seeds. The seeds were then placed in the mixer bowl and processing carried out until multiparticulates of a desired size were obtained. The contents of the bowl were then discharged and sieved to collect the 0.5–2.0 mm sieve fraction.

EXAMPLE 2

The procedure of Example 1 was repeated but the collected sieve fraction was blended in a conventional blender with 0.006 kg talc for 5 minutes; 0.004 kg magnesium stearate is then added and the blending continued for 3 minutes. The blend was then discharged and compressed using a 4 mm×8 mm capsule-shaped tooling on a F3 tablet machine. The resulting tablet had a hardness of 1.7 kp, a thickness of 2.8–3.0 mm and a friability of <1.0% w/w and the following composition:

| CONSTITUENT | MG/TABLET | % W/W |
|---|---|---|
| Diamorphine Hydrochloride | 40.0 | 47.6 |
| Hydrogenated Vegetable Oil | 40.0 | 47.6 |
| Talc | 2.40 | 2.86 |
| Magnesium Stearate | 1.6 | 1.91 |
| TOTAL | 84 | |

Reference Example 1

The dissolution rates of the resulting multiparticulates and tablets, measured respectively by the Ph. Eur. Basket or Paddle method at 100 rpm in either phosphate or acetate buffer, were as follows:

| | % DIAMORPHINE HCL RELEASE | | |
|---|---|---|---|
| TIME (HRS) | Multiparticulates Basket/Phosphate Buffer | Tablets Paddle/Phosphate Buffer | Tablets Paddle/Acetate Buffer |
| 1 | 30 | — | 24 |
| 2 | 44 | 35 | 35 |
| 3 | 54 | 41 | 43 |
| 4 | 62 | 47 | 49 |
| 6 | 70 | 57 | 59 |
| 8 | 78 | 64 | 67 |
| 12 | 87 | 75 | 78 |
| 16 | 92 | 84 | 86 |

Reference Example 2

The diamorphine hydrochloride content and the content of related substances was evaluated during storage at 30° C. over three months, the storage being in a polypropylene container with a polyethylene lid, with the following result:

| PRODUCT | INITIAL ANALYSIS (mg) | 3 MONTHS STORAGE (mg) | 6 MONTHS STORAGE (mg) |
|---|---|---|---|
| Diamorphine HCL | 38.7 | 38.9 | 40.1 |
| 6-0-acetylmorphine | 0.5 | 0.5 | 0.5 |
| Morphine HCL | 0.0 | 0.0 | 0.0 |

The dissolution rate of the tablets was measured by the Ph. Eur. Paddle Method at 100 rpm in pH 4.5 acetate buffer directly after preparation and after three months storage at 30° C., with the following result:

| | % DIAMORPHINE HCl RELEASED | | |
|---|---|---|---|
| TIME (HRS) | Initial Analysis | 3 Months | 6 Months |
| 1 | 24 | 22 | 22 |
| 2 | 36 | 32 | 32 |
| 3 | 44 | 41 | 39 |
| 4 | 50 | 47 | 45 |
| 5 | 55 | 52 | 51 |
| 6 | 59 | 57 | 55 |
| 7 | 64 | 61 | 59 |
| 8 | 68 | 65 | 63 |
| 9 | 70 | 68 | 66 |
| 10 | 73 | 71 | 69 |
| 11 | 76 | 74 | 71 |
| 12 | 79 | 77 | 74 |
| 13 | 81 | 80 | 76 |
| 14 | 83 | 81 | 78 |

-continued

| | % DIAMORPHINE HCl RELEASED | | |
|---|---|---|---|
| TIME (HRS) | Initial Analysis | 3 Months | 6 Months |
| 15 | 86 | 84 | 80 |
| 16 | 87 | 86 | 82 |
| 17 | 89 | 87 | 84 |
| 18 | 91 | 90 | 86 |
| 19 | NR | 91 | 87 |
| 20 | NR | 92 | 89 |

Comparative Example 1

| TABLET FORMULATION | MG/TABLET |
|---|---|
| Diamorphine hydrochloride | 10.0 |
| Lactose anhydrous | 90.0 |
| Hydroxyethylcellulose - (Natroxol 250HX) | 10.0 |
| Purified Water | q.s. |
| Cetostearyl alcohol (Dehydagwax) | 35.0 |
| Talc | 3.0 |
| Magnesium Stearate | 2.0 |
| TOTAL | 150.0 |

The diamorphine hydrochloride, lactose and hydroxyethyl cellulose were blended in a Collette Gral high speed mixer or equivalent. Water was added and the powder blend granulated by operating the mixer.

The resulting granulate was partially dried in fluid bed drier with an inlet air temperature of 60° C. The partially dried granulate was passed through a 12 mesh screen, then completely dried and passed through a 16 mesh screen.

The granules, while still warm were blended with molten cetostearyl alcohol at 65° C. using a mixer.

The resulting granules were cooled and passed through a 16 mesh screen, blended with the appropriate amounts of talc and magnesium stearate using a suitable blender and compressed into tablets on a suitable tableting machine using 7.14 mm diameter deep concave tooling.

The dissolution rate of the resulting tablets, measured by USP Paddle at 150 rpm in distilled water was:

| TIME (HR) | % DIAMORPHINE RELEASED |
|---|---|
| 1 | 54 |
| 2 | 71 |
| 3 | 83 |
| 4 | 89 |
| 5 | 95 |
| 6 | 99 |
| 7 | 100 |

The diamorphine-hydrochloride content of the tablets was evaluated during storage at room temperature, 30° C. and 30° C./80% relative humidity with the following results:

| | STORAGE TEMPERATURE DIAMORPHINE HCl CONTENT (mg/TABLET) | | |
|---|---|---|---|
| STORAGE TIME (MONTHS) | ROOM TEMPERATURE | 30° C. | 30° C./80% RH |
| 0 | 10.2 | — | — |
| 1 | 10.1 | 9.5 | 9.4 |
| 3 | 10.6 | 9.8 | 9.8 |
| 6 | 9.5 | 7.0 | 6.3 |

Comparative Example 2

| TABLET FORMULATION | MG/TABLET |
|---|---|
| Diamorphine hydrochloride | 30.0 |
| Lactose anhydrous | 70.0 |
| Hydroxyethylcellulose - (Natroxol 25OHX) | 10.0 |
| Purified Water | q.s. |
| Cetostearyl alcohol (Dehydagwax) | 35.0 |
| Talc | 3.0 |
| Magnesium Stearate | 2.0 |
| TOTAL | 150.0 |

The tablets were prepared from the above constituents and tested using the procedures described in Comparative Example 1.

The dissolution rates observed were as follows:

| TIME (HRS) | % DIAMORPHINE RELEASED |
|---|---|
| 1 | 52 |
| 2 | 68 |
| 3 | 81 |
| 4 | 91 |
| 5 | 96 |
| 6 | 99 |
| 7 | 100 |

The diamorphine hydrochloride content of the tablets under the various storage conditions was found to be as follows:

| | STORAGE TEMPERATURE DIAMORPHINE HCl CONTENT (mg/TABLET) | | |
|---|---|---|---|
| STORAGE TIME (MONTHS) | ROOM TEMPERATURE | 30° C. | 30° C./80% RH |
| 0 | 33.2 | — | — |
| 1 | 30.7 | 31.4 | 29.6 |
| 3 | 30.3 | 30.0 | 30.1 |
| 6 | 29.4 | 28.2 | 28.3 |

It can be seen that the formulations of diamorphine in accordance with the invention provide for a controlled-release of diamorphine for twice or once-a-day dosing. This is not possible with a formulation of diamorphine in a conventional controlled-release matrix.

The foregoing examples also show that formulations of the invention have unexpectedly superior storage stability compared with a formulation using the conventional controlled-release matrix both in terms of stability of the absolute quantity of active ingredient and degradation products, and the in-vitro release rates of diamorphine or salt.

The examples provided above are not meant to be exclusive. Many other variations of the present invention would be obvious to those skilled in the art, and are contemplated to be within the scope of the appended claims.

It is claimed:

1. A controlled release, storage stable solid pharmaceutical preparation comprising a controlled release matrix comprised of a particulate, hydrophobic, fusible carrier or diluent having a melting point ranging from about 35° to 150° C., and an effective amount of diamorphine or a pharmaceutically acceptable salt thereof, said controlled release matrix in a form selected from the group consisting of multiparticulates, granules and controlled release seeds, that is suitable for administration at time intervals ranging from about 12 to about 24 hours, said pharmaceutical preparation being prepared without water and retaining substantially all of the incorporated diamorphine after at least six months of storage at 30° C., relative to a preparation that has not undergone said storage, said preparation exhibiting no substantial difference in in-vitro dissolution rate, as measured by Ph. European Paddle method at 100 rpm in 900 ml of aqueous buffer at pH 4.5 at 37° C., relative to said preparation that has not undergone said storage.

2. The controlled release, storage stable solid pharmaceutical preparation of claim 1, further comprising conventional capsulating excipients.

3. The controlled release, storage stable solid pharmaceutical preparation of claim 1 comprising a tablet comprising said multiparticulates, granules or controlled-release seeds in compressed form.

4. The preparation of claim 3, comprising conventional tableting excipients.

5. The controlled-release, storage stable solid pharmaceutical preparation according to claim 1 which has a dissolution rate as follows:

| TIME (HR) | % DIAMORPHINE RELEASED |
| --- | --- |
| 1 | 0–70 |
| 2 | <80 |
| 4 | 10–100 |
| 12 | 40–100 |
| 16 | 50–100 |

6. The controlled release, storage stable solid pharmaceutical preparation according to claim 1, wherein the release rate is as follows:

| TIME (HR) | % DIAMORPHINE RELEASED |
| --- | --- |
| 1 | 10–70 |
| 2 | 15–80 |
| 4 | 30–100 |
| 6 | 40–100 |
| 12 | 60–100 |
| 16 | 70–100 |

7. The controlled release, storage stable solid pharmaceutical preparation according to claim 1, wherein the release rate is as follows:

| TIME (HR) | % DIAMORPHINE RELEASED |
| --- | --- |
| 1 | 0–50 |
| 4 | 10–80 |
| 8 | 30–100 |
| 12 | 40–100 |
| 16 | 50–100 |

8. A preparation according to claim 1, comprising an amount of diamorphine or salt thereof sufficient for up to 24 hours dosing.

9. A preparation according to claim 1, which provides for controlled-release of the diamorphine or salt such that it is suitable for 12 hourly administration.

10. A preparation according to claim 1, which provides for controlled-release of the diamorphine or salt such that it is suitable for 24 hourly administration.

11. A storage stable sustained-release diamorphine pharmaceutical preparation prepared by a process comprising the steps of mechanically working, in a high shear mixer, and without water, a mixture of diamorphine or pharmaceutically active salt thereof in particulate form and a particulate, hydrophobic, fusible carrier or diluent having a melting point from 35° to 150° C., at a speed and energy input which allows the carrier or diluent to melt or soften whereby it forms a matrix of hydrophobic fusible carrier or diluent containing an effective amount of diamorphine or salt thereof dispersed therein to produce a storage stable, sustained-release pharmaceutical preparation.

12. The pharmaceutical preparation of claim 11, wherein said process further comprises the step of adding to said mixture a release modifying component comprising a water soluble, fusible material or a particulate, soluble or insoluble organic or inorganic material.

13. Pharmaceutical sustained-release multiparticulates containing diamorphine or a salt thereof prepared by a process comprising the steps of:

(a) mechanically working in a high-shear mixer, a mixture of an effective amount of diamorphine or a salt thereof in particulate form and a particulate, hydrophobic, fusible carrier or diluent having a melting point from 35° to 150° C., without water, at a speed and energy input which allows the carrier or diluent to melt or soften, whereby it forms agglomerates; and (b) breaking down from step (a) said agglomerates into a plurality of sustained-release multiparticulates.

14. A process according to claim 13, wherein said mixture further comprises a release modifying component comprising a water soluble fusible material, or a particulate soluble or insoluble organic or inorganic material.

15. A process according to claim 13, further comprising continuing mechanically working optionally with a further addition of low percentage of the carrier or diluent.

16. A process according to claim 13, comprising repeating step (b) up to five times.

17. A process according to claim 11, wherein the product is sieved or milled to obtain multiparticulates, granules or controlled-release seeds or particles of a desired size range.

18. A process according to claim 13, wherein said multiparticulates or granules are further processed by filling into capsules.

19. A process according to claim 13, wherein said multiparticulates, granules or controlled-release seeds or particles are compressed into tablets.

20. A process according to claim 13, comprising mixing said multiparticulates, granules or controlled-release seeds or particles, with conventional tableting excipients.

21. A method of treating a patient suffering from pain which comprises administering to the patient a storage stable, controlled release preparation comprising an effective amount of diamorphine or a pharmaceutically acceptable salt thereof and a controlled release matrix in a form selected from the group consisting of multiparticulates, granules and controlled release seeds, that is suitable for administration at time intervals ranging from about 12 to about 24 hours, said pharmaceutical preparation being prepared without water and retaining substantially all of the incorporated diamorphine after at least six months of storage at 30° C., relative to a preparation that has not undergone said storage, said preparation exhibiting no substantial difference in in-vitro dissolution rate, as measured by Ph. European Paddle method at 100 rpm in 900 ml of aqueous buffer at pH 4.5 at 37° C., relative to said preparation that has not undergone said storage.

22. A method of treating a heroin addict by maintenance therapy, which comprises administering to the addict a storage stable preparation comprising an effective amount of diamorphine or a pharmaceutically acceptable salt thereof and a controlled release matrix in a form selected from the group consisting of multiparticulates, granules and controlled release seeds, that is suitable for administration at time intervals ranging from about 12 to about 24 hours, said pharmaceutical preparation being prepared without water and retaining substantially all of the incorporated diamorphine after at least six months of storage at 30° C., relative to a preparation that has not undergone said storage, and that shows no substantial difference in in-vitro dissolution rate, as measured by Ph. European Paddle method at 100 rpm in 900 ml of aqueous buffer at pH 4.5 at 37° C., relative to said preparation that has not undergone said storage.

23. The storage stable, controlled release preparation of claim 1 wherein the preparation is storage stable for at least three months.

24. The storage stable, controlled release preparation of claim 1 wherein the preparation shows no substantial change in the content of a substance selected from the group consisting of diamorphine, 6-O-acetylmorphine, morphine or a salt thereof, during storage at 30° C. for at least six months.

25. The preparation of claim 1, wherein said preparation comprises a release modifying component selected from the group consisting of a water-soluble fusible material, a particulate soluble and an insoluble organic or inorganic material.

26. The preparation of claim 1, comprising said controlled release matrix enclosed in a capsule suitable for oral administration.

* * * * *